US011557380B2

(12) United States Patent
Clark et al.

(10) Patent No.: US 11,557,380 B2
(45) Date of Patent: Jan. 17, 2023

(54) RECURRENT NEURAL NETWORK TO DECODE TRIAL CRITERIA

(71) Applicant: International Business Machines Corporation, Armonk, NY (US)

(72) Inventors: Adam Clark, Mantorville, MN (US); Eric W Will, Rochester, MN (US)

(73) Assignee: MERATIVE US L.P., Ann Arbor, MI (US)

( * ) Notice: Subject to any disclaimer, the term of this patent is extended or adjusted under 35 U.S.C. 154(b) by 203 days.

(21) Appl. No.: 16/278,260

(22) Filed: Feb. 18, 2019

(65) Prior Publication Data

US 2020/0265927 A1 Aug. 20, 2020

(51) Int. Cl.
*G16H 10/20* (2018.01)
*G06N 3/08* (2006.01)
*G06N 3/04* (2006.01)
*G06F 40/205* (2020.01)

(52) U.S. Cl.
CPC .......... *G16H 10/20* (2018.01); *G06F 40/205* (2020.01); *G06N 3/0445* (2013.01); *G06N 3/08* (2013.01)

(58) Field of Classification Search
CPC ..................................................... G16H 10/20
See application file for complete search history.

(56) References Cited

U.S. PATENT DOCUMENTS

| 8,095,389 B2 | 1/2012 | Dalton | |
| 2020/0258629 A1* | 8/2020 | Ahmad | G16H 50/20 |

FOREIGN PATENT DOCUMENTS

| WO | 2014025765 A2 | 2/2014 |
| WO | 2017122785 A1 | 7/2017 |

OTHER PUBLICATIONS

Geraci, J., Wilansky, P., de Luca, V., Roy, A., Kennedy, J., & Strauss, J. (Aug. 2017). Applying deep neural networks to unstructured text notes in electronic medical records for phenotyping youth depression. Evidence Based Mental Health, 20(3), 83-87. (Year: 2017).*
Mitchel, J. T., Kim, Y. J., Choi, J., Park, G., Cappi, S., Horn, D., Kist, M., & D'Agostino, R. B., Jr. (2011). Evaluation of data entry errors and data changes to an electronic data capture clinical trial database. Drug Information Journal, 45(4), 421-430) (Year: 2011).*
Fragkiadaki et al, "Recurrent Network Models for Human Dynamics,"berkeley.edu, 9 pages.

(Continued)

*Primary Examiner* — Robert A Sorey
*Assistant Examiner* — Kristine K Rapillo
(74) *Attorney, Agent, or Firm* — Patterson + Sheridan, LLP

(57) ABSTRACT

A method and apparatus for providing curated criteria to identify one or more candidates for a clinical trial is disclosed. A computer processor identifies a first input criterion for the clinical trial. The processor employs a trained first recurrent neural network (RNN) configured as an encoder to encode the first input criterion. The encoder extracts key features of the medical condition of the patient. The processor employs a trained second RNN configured as a decoder to generate a curated output criterion by processing the encoded first input criterion based on the derived key features. The processor employs a machine learning model to ingest the curated output criterion to identify the one or more candidates for the clinical trial.

20 Claims, 6 Drawing Sheets

(56) References Cited

OTHER PUBLICATIONS

Lipton et al, "A Critical Review of Recurrent Neural Networks for Sequence Learning," arXiv:1506.00019v4 [cs.LG] Oct. 17, 2015, 38 pages.

Authors et. al.: Disclosed Anonymously, "Method for Efficiently Selecting Patients for Clinical Trials," IP.com No. IPCOM000232370D | IP.com Electronic Publication Date: Nov. 4, 2013 | 3 pages.

Authors et. al.: Disclosed Anonymously, "Extracting Point of Interest Information from Query Logs," IP.com No. IPCOM000252095D | IP.com Electronic Publication Date: Dec. 15, 2017 | 33 pages.

Authors et. al.: Disclosed Anonymously, "Modeling Disease Incidence and Progression Using Deep Neural Networks," IP.com No. IPCOM000252181D | IP.com Electronic Publication Date: Dec. 20, 2017 | 5 pages.

\* cited by examiner

RECURRENT NEURAL NETWORK TO DECODE TRIAL CRITERIA

BACKGROUND

The present invention relates to neural networks, and more specifically, to employing neural networks to format clinical trial textual criteria.

A significant task in conducting clinical trials for medical treatments is to determine a set of patients who are eligible for the clinical trials. Clinical trials generally include criteria defining one or more characteristics of patients who may be eligible for a trial. The eligibility criteria often take the form of single sentences, multiple-sentences, and logical statements. Examples include positive declarative statements, e.g., "patient A must have a lab test with value B as a result", or "patient A must be age x-y", or "patient A must have this genetic marker". Other examples include exclusionary statements, e.g., "Patient A cannot be pregnant", or "patient A cannot be on dialysis".

Techniques for determining the set of eligible patients for a clinical trial include manual data mining methods of hundreds or thousands of textual statements/criteria. There are several problems with current data mining methods for mining textual criteria. For example, the criteria in the form of textual statements are frequently incorrect, inaccurate, or unclear. Inaccurate criteria renders it difficult to successfully ingest the criteria into a computer for identifying the set of eligible patients for a clinical trial, since inaccurate input data results in corresponding inaccurate conclusions. If errors in the input data are not removed, the resulting data mining methods are not trustworthy. This results in the number of eligible patients being fewer than the total set of patients who would be otherwise eligible had the input criteria been formatted in a machine-readable form. Current data mining systems require manual curation of the data to correct these defects, which is impractical for large data sets, and may be still prone to inaccuracy.

SUMMARY

According to one embodiment, a method for providing curated criteria to identify one or more candidates for a clinical trial is disclosed. A computer processor identifies a first input criterion for the clinical trial. The first input criterion includes a first textual statement pertaining to a medical condition of a patient. The processor employs a trained first recurrent neural network (RNN) configured as an encoder to encode the first input criterion. The encoder extracts key features of the medical condition of the patient and converts the key features to a numerical representation. The processor employs a trained second RNN configured as a decoder to generate a curated output criterion by processing the encoded first input criterion. The curated output criterion includes a second textual statement pertaining to the medical condition of a patient derived from the key features. The processor employs a machine learning model to ingest the curated output criterion to identify the one or more candidates for the clinical trial. Ingesting includes applying natural language processing to the curated output criterion to extract concepts and logical relationships pertaining to the medical condition of the patient.

According to one embodiment, a system is disclosed. The system includes a processor and memory storing program code, which, when executed on the processor, performs operations for providing curated criteria to identify one or more candidates for a clinical trial. The operations include identifying a first input criterion for the clinical trial. The first input criterion includes a first textual statement pertaining to a medical condition of a patient. The operations further include employing a trained first recurrent neural network (RNN) configured as an encoder to encode the first input criterion. The encoder extracts key features of the medical condition of the patient and converts the key features to a numerical representation. The operations further include employing a trained second RNN configured as a decoder to generate a curated output criterion by processing the encoded first input criterion. The curated output criterion includes a second textual statement pertaining to the medical condition of a patient derived from the key features. The operations further include employing a machine learning model to ingest the curated output criterion to identify the one or more candidates for the clinical trial. Ingesting includes applying natural language processing to the curated output criterion to extract concepts and logical relationships pertaining to the medical condition of the patient.

According to one embodiment, a computer program product for providing curated criteria to identify one or more candidates for a clinical trial is disclosed. The computer program product comprises a computer-readable storage medium having computer-readable program code embodied therewith, the computer-readable program code executable by one or more computer processors. The one or more processors identify a first input criterion for the clinical trial. The first input criterion comprises a first textual statement pertaining to a medical condition of a patient. The one or more processors encode the first input criterion. The encoder extracts key features of the medical condition of the patient and converts the key features to a numerical representation. The one or more processors generate a curated output criterion by processing the encoded first input criterion with a trained second RNN configured as a decoder. The curated output criterion comprises a second textual statement pertaining to the medical condition of a patient derived from the key features. The one or more processors ingest the curated output criterion into a machine learning model to identify the one or more candidates for the clinical trial. Ingesting comprises applying natural language processing to the curated output criterion to extract concepts and logical relationships pertaining to the medical condition of the patient.

DETAILED DESCRIPTION

Figure 1:
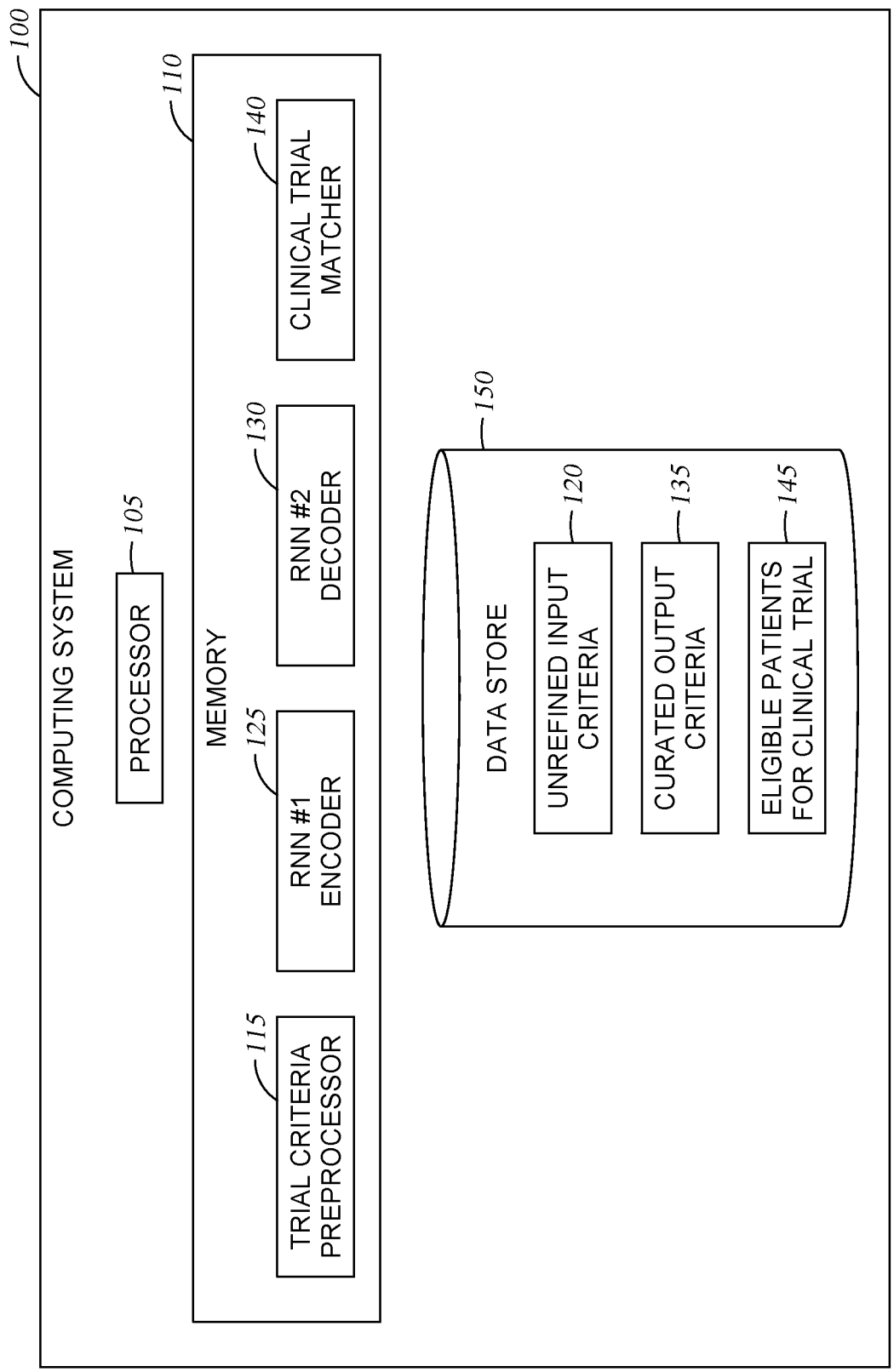
FIG. 1 illustrates a computing system for providing curated output criteria from unrefined input criteria to identify one or more candidates for a clinical trial, according to one embodiment described herein.

As noted above, accurate clinical trial patient matching is a task that is prone to inaccuracy due to errors or lack of clarity in input criteria. The input criteria may be written poorly, have inconsistencies, or have logical or syntactical errors. Humans reading such criteria may still be able to recognize the criteria, but natural language processing (NLP) applications often operate on literal meaning and may not recognize the input criteria. For example, a person may evaluate the statement: "a patient must be male and female." A NLP application reading this statement may conclude that the patient is both male AND female, but a human may correctly interpret this statement to read that "a patient must be male OR female." In addition to logical errors, the input criteria may have grammatical and typographical mistakes, or may be stated in sentence fragments, or contain unexpanded acronyms. Accordingly, a cognitive system employing a machine learning method to qualify patients for a clinical trial would miss important pieces of information useful to accurately parse the input criteria and understand what the input criteria is intending to indicate. Input criteria that are not clear, no-logically formed, or contain errors are herein referred to as "unrefined input criteria."

Embodiments of the present disclosure attempt to preprocess or convert the unrefined input to output criteria whose logical structure and words are recognizable by a machine learning method of a computer to aid in the selection of patients that may be eligible for a clinical trial based on the preprocessed input criteria. The preprocessing is effected by applying a pair of recurrent neural networks configured as an encoder and corresponding decoder trained to convert unrefined input criteria into parse-able and computer readable output criteria. The parse-able and computer-readable output criteria exiting the decoder are herein referred to as "curated output criteria" or "ground truth output criteria."

Artificial neural networks are machine learning models inspired by the operating principles of the neural network of the human brain and have been widely applied to problems of classification and function approximation. A deep learning artificial neural network is part of a broader family of machine learning methods based on learning data representations, as opposed to task-specific algorithms. Deep learning is a class of machine learning algorithms that use a cascade of multiple layers of nonlinear processing units for feature extraction and transformation of input data. Each successive layer of the multiple layers uses the output from the previous layer as input. The multiple layers are then trained to learn a representation (encoding) of a set of input data, typically for the purpose of dimensionality reduction in an unsupervised (e.g., pattern analysis) manner.

A regular (non-recurrent) deep learning neural network is a generic machine learning algorithm that takes in a list of numbers and calculates a result (based on previous training). But like most machine learning algorithms, neural networks are stateless. A list of numbers may be passed into the neural network and the neural network calculates a result. If the same numbers are input to the neural network again, the neural network will always calculate the same result. It has no memory of past calculations. In other words, 2+2 always equals 4.

Embodiments of the present disclosure employ an artificial neural network architecture known as a recurrent neural network (RNN). A recurrent neural network (or RNN for short) is an altered version of a neural network where the previous state of the neural network is one of the inputs to the next calculation. This means that previous calculations change the results of future calculations. This stateful property allows RNNs to learn patterns in a sequence of data. For example, an RNN can predict the next most likely word in a sentence based on the first few words: RNNs are useful any time learning patterns in data are needed. An RNN can be configured as an encoder. Because the RNN has a "memory" of each word that passed through it, the encoder may examine a repeated number of similar sentences containing input words within a window of context of words surrounding the input words. From the input words and the context of words, the encoder extracts key features of the input sentence and calculates a set of numerical values that represents all the words in the sentence.

An encoder provides a way to represent an entire sentence as a set of unique numbers. The meaning of each number in the set of numbers is not known. However, as long as each sentence is uniquely identified by its own set of numbers, it is not necessary to know exactly how those numbers were generated.

In example of the present disclosure, two RNNs are placed one after another end-to-end. The first RNN could generate the encoding that represents a sentence. Then the second RNN could take that encoding and perform the same logic in reverse to decode the original sentence again. Initially, if an untrained encoder-decoder pair is not trained with grammatically and logically correct sentences, then corresponding output of the encoder-decoder pair would also contain errors or unclear meaning. However, an encoder-decoder pair can be trained with incorrect input sentences but output grammatically and logically correct versions of the input sentences by employing one of many neural known network training techniques involving adjusting weights of the nodes that constitute the encoder-decoder neural networks. Accordingly, a trained encoder can be configured to convert an unrefined clinical trial input criterion it into a numerical representation that encapsulates all of the unique characteristics (e.g. key features) of the input criterion within the context of the sentence in which it resides, and then the decoder can decode the key features back into a "corrected" output criterion. By employing an encoder-decoder pair, the unrefined input criteria may be augmented into "curated output criteria" to allow a machine learning method to qualify more patients for a trial. The trial qualification scoring of the machine learning model improves, is more consistent, and engenders more confidence in the results and, accordingly, permits the machine learning method to enroll more patients.

In an example, an unrefined input criterion, such as: "Measurable or non-measurable disease according to RECIST v1.1" is inputted into the encoder/decoder engine, and is trained to learn that the output of the decoder should read: "patient has measurable disease or patient has non-measurable disease." Another example may be: "MDS patients with: 10.% to 20.3% blas cells are eligible;" being converted to: "Myelodysplastic syndrome patients with 10% to 20.3% blast cells are eligible." In the latter example:

Acronyms are expanded.

The excessive/confusing "." following "10" is removed. The typographical error "blas" is changed to "blast".

The final ";" is converted to "." to minimize confusion about sentence boundaries.

FIG. 1 illustrates a computing system 100 for providing curated output criteria 135 from unrefined input criteria 120 to identify one or more candidates for a clinical trial, according to one embodiment described herein. The computing system 100 includes a processor 105, (main) memory 110, and a persistent data store 150. The processor 105 constructs a trail criteria preprocessor 115, an encoder 125, a decoder 130, and a clinical trial matcher 140 by fetching instructions of a program stored in the data store 150 and loading the trail criteria preprocessor 115, an encoder 125, a decoder 130, and a clinical trial matcher 140 into the main memory 110. The processor 205 represents one or more processing elements that each may include multiple processing cores. Using the processor 205, the trial criteria preprocessor 115 identifies a first unrefined input criterion 120 for the clinical trial by retrieving the first unrefined input criterion 120 from the data store 150 and loading the first unrefined input criterion 120 into the main memory 110. The trial criteria preprocessor 115 directs a trained first recurrent neural network (RNN) configured as an encoder 125 to encode the first unrefined input criterion 120. The trial criteria preprocessor 115 directs a trained second RNN configured as a decoder 130 to generate a curated output criterion 135 and stores the curated output criterion 135 back into the data store 150. The clinical trial matcher 140 ingests the curated output criterion 135 and applies a machine learning model to identify the one or more candidates for the clinical trial. The machine learning model applies NLP to the curated output criterion 135 to extract concepts and logical relationships pertaining to the medical condition of the patient. The machine learning model compares the extracted concepts and logical relationships pertaining to the medical condition of the patient against known patient characteristics and/or medical records of an acceptable candidate for the clinical trial to determine whether to declare the patient eligible for the clinical trial. The clinical trial matcher 140 then outputs a list of eligible patients for the clinical trial 145 and stores the list in the data store 150.

Figure 2:
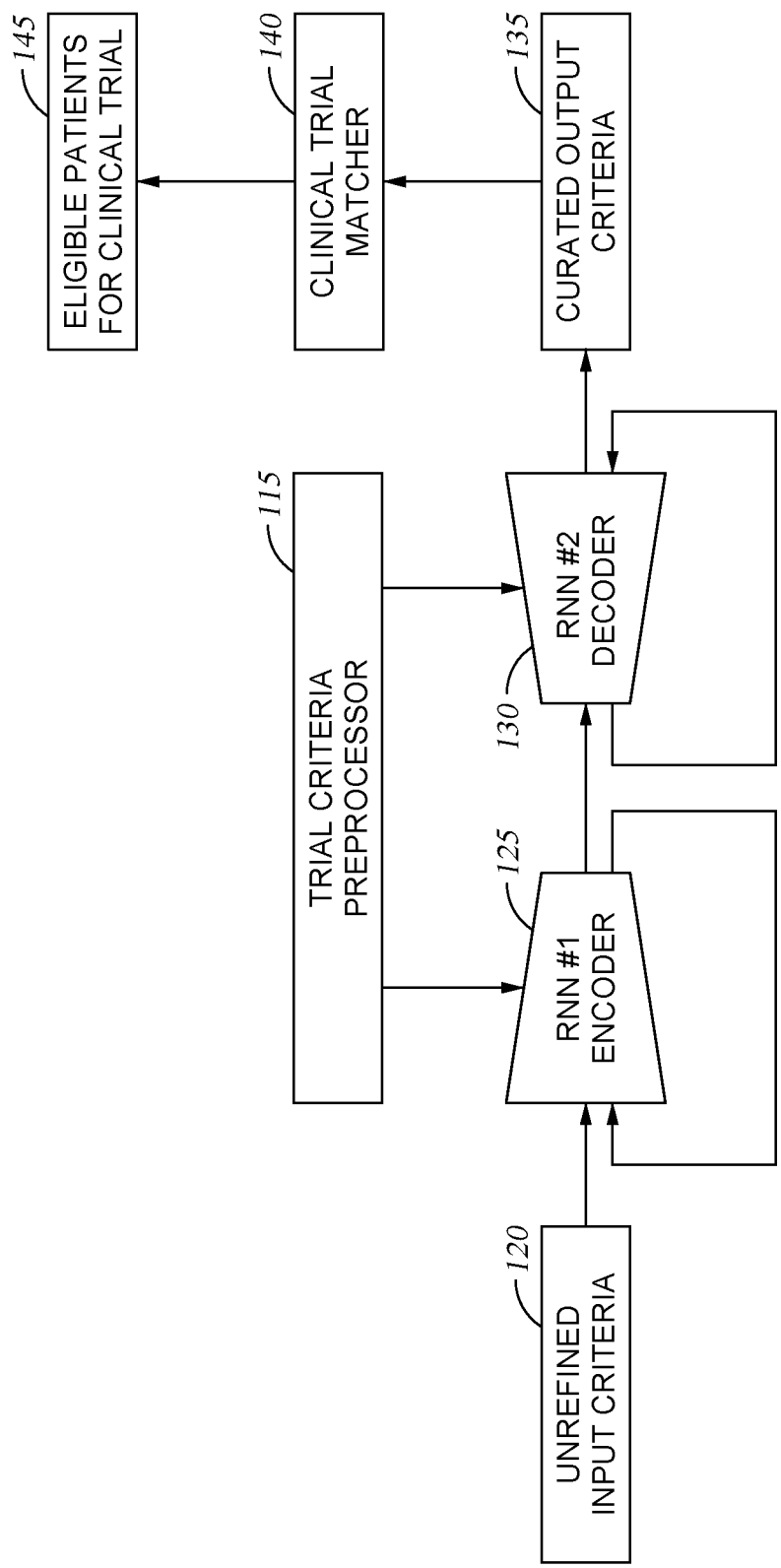
FIG. 2 illustrates a program architecture for providing curated output criteria from unrefined input criteria to identify one or more candidates for a clinical trial, according to one embodiment described herein.

FIG. 2 illustrates a program architecture 200 for providing curated output criteria 135 from unrefined input criteria 120 to identify one or more candidates for a clinical trial, according to one embodiment described herein. The trial criteria preprocessor 115 identifies an unrefined input criterion 120 for the clinical trial. The unrefined input criterion 120 includes an input textual statement pertaining to medical conditions of a patient. The input textual statement may include one or more errors in spelling, syntax, grammar, or logic, or may not have errors be have unclear language that is not recognizable to a machine learning model (within the clinical trial matcher 140). The trial criteria preprocessor 115 directs the trained encoder 125 to encode the unrefined input criterion 120. The encoder 125 employs a minimum size window of text surrounding each word of an unrefined input criterion 120 to provide the encoder 125 with a context for the unrefined input criterion 120. The encoder 125 extracts key features of the medical condition of the patient and converts the key features to numerical representations of the key features 314 of the unrefined input criterion 120. The key features include a set of attributes comprising textual alphanumerical words, punctuation, and a set of logical rules pertaining to the set of attributes.

The trial criteria preprocessor 115 directs the trained decoder 130 to generate a curated output criterion 135. The curated output criterion 135 comprises a second textual statement pertaining to the medical condition of the patient derived from the key features. The second textual statement has no errors in spelling, syntax, grammar, and logic. The curated output criterion 135 adheres to a preferred set of logical rules and format. The trained decoder 130 generates the curated criterion 135 by assembling the extracted key features into a parse-able and logically consistent text string to render the curated output criterion 135 evaluate-able by a machine learning model within the clinical trial matcher 140.

The clinical trial matcher 140 ingests the curated output criterion 135 to identify an associated patient/candidate for the clinical trial. The machine learning model applies natural language processing to the curated output criterion 135 to extract concepts and logical relationships pertaining to the medical condition of the patient. The machine learning model compares the extracted concepts and logical relationships pertaining to the medical condition of the patient against known patient characteristics and/or medical records of an acceptable candidate for the clinical trial to determine whether to declare the patient eligible for the clinical trial. The machine learning model of the clinical trial matcher 140 outputs a list of eligible patients for the clinical trial 145.

Figure 3:
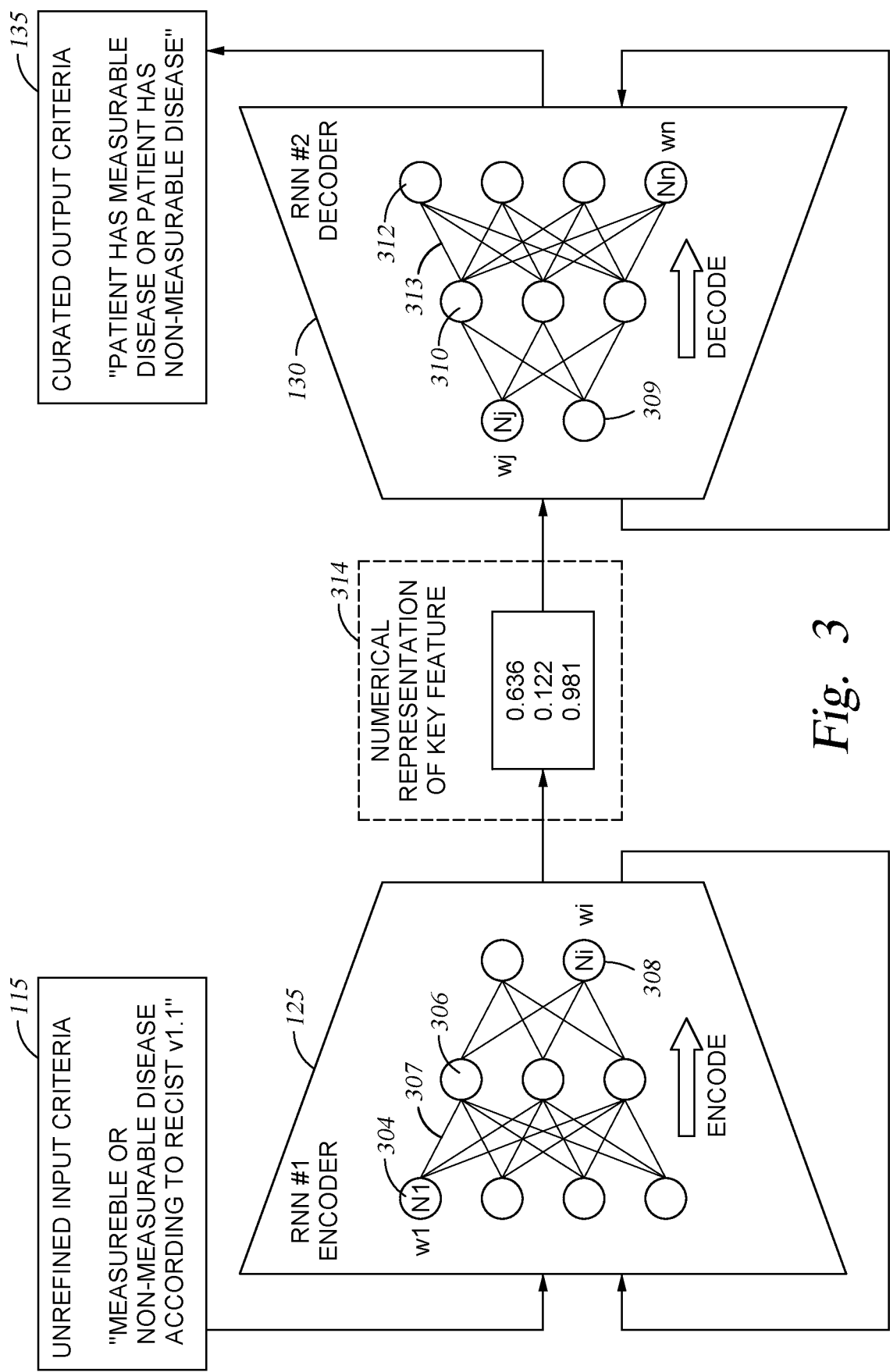
FIG. 3 illustrates an internal architecture of the encoder-decoder pair of recurrent neural networks employed in embodiments of the present disclosure and a technique for training the encoder-decoder pair.

FIG. 3 illustrates an internal architecture of the encoder 125-decoder 130 pair of recurrent neural networks employed in embodiments of the present disclosure and a technique for training the encoder 125-decoder 130 pair. The input data to the encoder is a set of unrefined input criteria 120 (e.g., "Measurable or non-measurable disease according to RECIST v1.1"). The encoder 125 may comprise an input layer 304 of neural nodes N1-Ni, one or more hidden layers 306 of neural nodes N1-Ni, an output layer 308 of neural nodes N1-Ni, and a full set of connections 307 between the layers. Each of the nodes Ni-Ni in the encoder 125 has an associated weight w1-wi. The output layer 308 has the smallest number of nodes. The decreasing number of nodes in each successive layer of nodes 304, 306, 308 helps the encoder 125 find a numerical representation of key features 314 of the unrefined input criterion 120. Similarly, the decoder 130 has an increasing number of nodes in a corresponding succession of layers 309, 310, 312 having nodes Nj-Nn, weights Wj-Wn, and a full set of connections 313 between the layers to expand the numerical representation to a curated output criterion 135 represented by a corresponding string (e.g., "patient has measurable disease or patient has non-measurable disease").

The encoder 125-decoder 130 is trained before use on real data. Training data includes a set of unrefined input criteria 120 and a corresponding set of already curated output criteria. The unrefined input criteria 120 are passed through the encoder 125 and the decoder 130 to produce partially curated output criteria that have one or more textual differences from corresponding curated output criterion 135. A training method for a neural network incrementally adjusts weights of the encoder 125-decoder 130 until the weights converge based on the determined one or more textual differences for the plurality of partially curated output criteria falls below a predetermined threshold.

Training a neural network (NN) (RNN or otherwise) usually involves feeding in the input to the NN, letting the NN produce some output, identifying/calculating the differences between the desired output and the actual output, and then using, for example, a back-propagation training algorithm. The back-propagation algorithm steps backwards through the various nodes of the NN to make small adjustments to each weight in the NN so that the NN more accurately produces the desired output.

In a training example employed in the system 100, the trial criteria preprocessor 115 identifies a plurality of unrefined input criteria 120. Each of the unrefined input criteria 120 comprises an unrefined textual statement pertaining to one or more medical conditions of one or more patients. The trial criteria preprocessor 115 identifies a plurality of curated output criteria 135. Each of the curated output criteria 135 comprises a curated textual statement pertaining to the one or more medical conditions of the one or more patients. The trial criteria preprocessor 115 encodes and decodes, using the encoder 125 and the decoder 130, each of the plurality of unrefined input criteria 120 into a corresponding plurality of partially curated output criteria 135, respectively. The trial criteria preprocessor 115 determines one or more textual differences between each of the partially curated output criteria and a corresponding curated output criterion 135. The trial criteria preprocessor 115 applies a training algorithm to the encoder 125 and the decoder 130 to incrementally adjust weights (e.g., $w_1$-$w_n$) of nodes (e.g., $N_1$-$N_n$) within the encoder 125 and the decoder 130 for each of the partially curated output criteria. In one embodiment, the training algorithm is a back propagation neural network training algorithm. If, the weights converge based on the determined one or more textual differences for the plurality of partially curated output criteria falling below a predetermined threshold, then processing ceases. If, the weights have not yet converged, then processing is repeated using the partially curated output criteria and the already curated output criterion 135 to re-adjust the weights until the weights converge. Accordingly, the encoder 125 and the decoder 130 are sufficiently trained.

In one embodiment, after a number of input/output criteria have been processed with the trained encoder 125 and decoder 130, the encoder 125 and the decoder 130 may be periodically retrained using the already processed input/output criteria.

By encoding and decoding the criteria with one or more RNNs, trial criteria can be normalized into a format that is best suited for ingestion into machine learning models contained within the clinical trial matcher 140. This process is automated to be far quicker and more accurate than manual intervention, which is the conventional approach.

Figure 4:
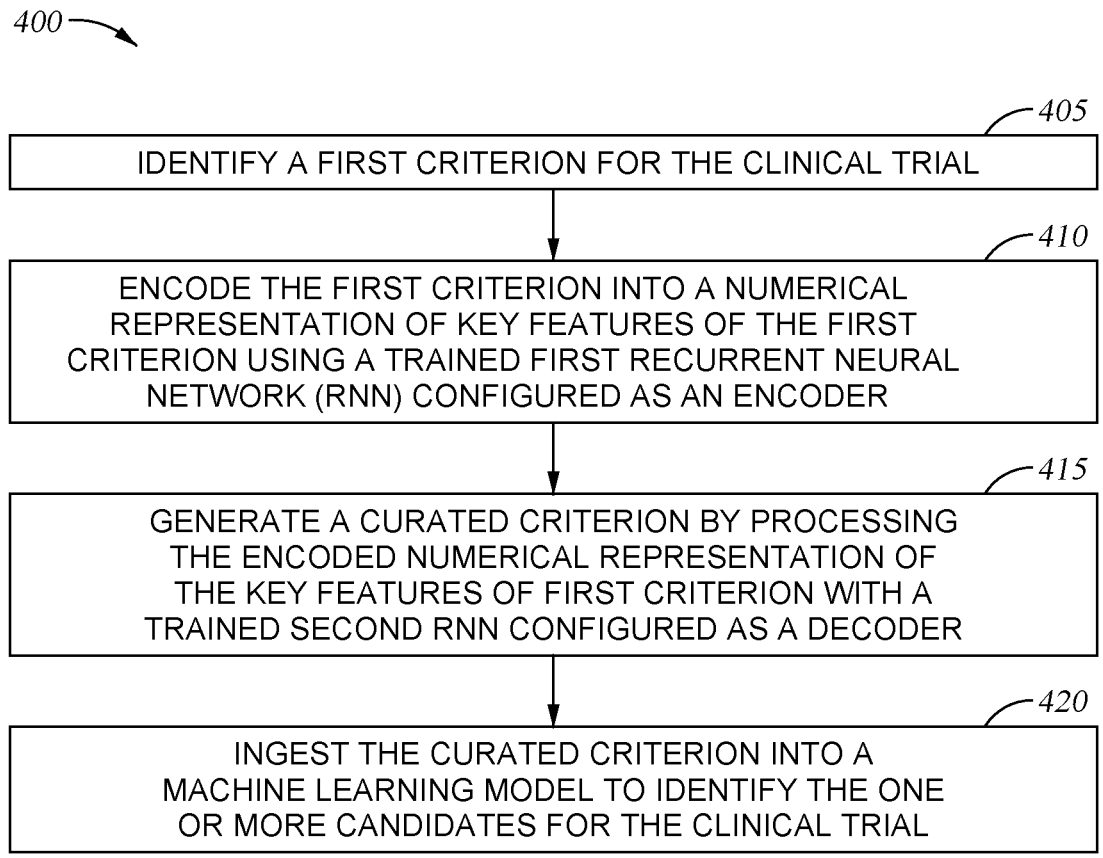
FIG. 4 illustrates one embodiment of a method for refining criteria to identify one or more candidates for a clinical trial.

FIG. 4 illustrates one embodiment of a method 400 for refining criteria to identify one or more candidates for a clinical trial. Method 400 can be performed by processing logic that can comprise hardware (e.g., circuitry, dedicated logic, programmable logic, microcode, etc.), software (e.g., instructions run on a processing device), or a combination thereof. In one embodiment, method 400 is performed by the trial criteria preprocessor 115 and the clinical trial matcher 140 of FIG. 2.

At block 405, the trial criteria preprocessor 115 identifies a first unrefined input criterion 120 for the clinical trial. The first unrefined input criterion 120 includes a first textual statement pertaining to a medical condition of a patient. The first textual statement may one or more errors in spelling, syntax, grammar, or logic, or may be unclear enough for recognition by a machine learning model. At block 410, the trial criteria preprocessor 115 directs a trained first recurrent neural network (RNN) configured as an encoder 125 to encode the first unrefined input criterion 120. The encoder 125 employs a minimum size window of text surrounding each word of the unrefined input criterion 120 to provide the encoder 125 with a context for the unrefined input criterion 120. The encoder 125 extracts key features of the medical condition of the patient and converts the key features 314 to a numerical representation. The key features include a set of attributes of the first statement comprising textual alphanumerical words, and punctuation, and a set of logical rules pertaining to the set of attributes.

At block 415, the trial criteria preprocessor 115 directs a trained second RNN configured as a decoder 130 to generate a curated output criterion 135. The curated output criterion 135 comprises a second textual statement pertaining to the medical condition of a patient derived from the key features. The second textual statement has no errors in spelling, syntax, grammar, and logic. The curated output criteria 135 adhere to a preferred set of logical rules and format. The trained decoder 130 generates the curated criterion by assembling the extracted key features into a criterion that is parse-able and is logically consistent to render the curated output criterion 135 evaluate-able by a machine learning model.

At block 420, the clinical trial matcher 140 ingests the curated output criterion 135 into a machine learning model contained therein to identify the one or more candidates for the clinical trial. The machine learning model applies natural language processing to the curated output criterion 135 to extract concepts and logical relationships pertaining to the medical condition of the patient. The machine learning model compares the extracted concepts and logical relationships pertaining to the medical condition of the patient against known patient characteristics and/or medical records of an acceptable candidate for the clinical trial to determine whether to declare the patient eligible for the clinical trial.

Figure 5:
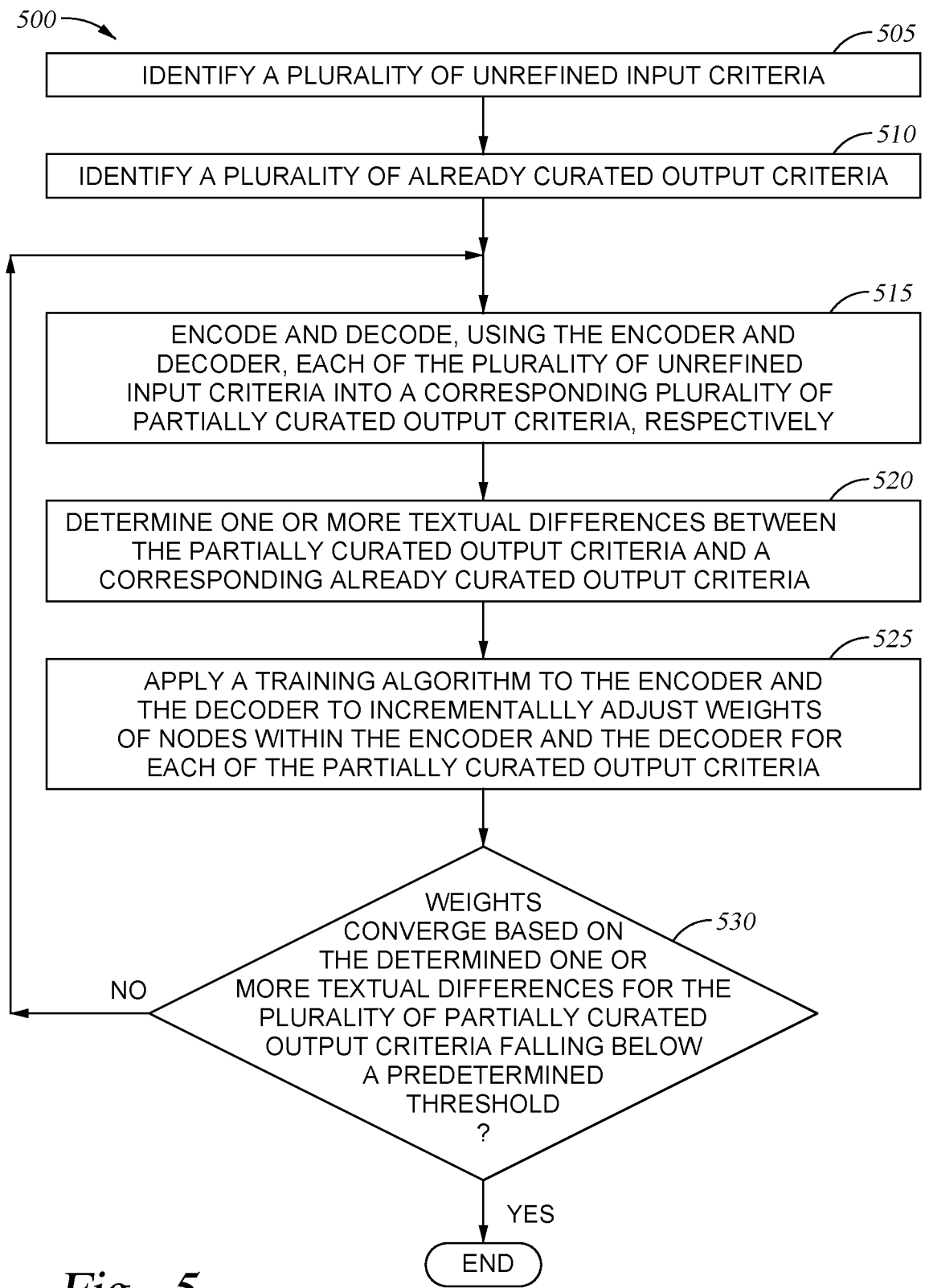
FIG. 5 illustrates one embodiment of a method for iteratively training the encoder and the decoder.

The encoder 125 and the decoder 130 are iteratively trained using a plurality of unrefined input criteria 120 associated with a plurality of clinical trials and a corresponding plurality of curated output criteria 135 associated with the plurality of clinical trials. FIG. 5 illustrates one embodiment of a method 500 for iteratively training the encoder 125 and the decoder 130. Method 500 can be performed by processing logic that can comprise hardware (e.g., circuitry, dedicated logic, programmable logic, microcode, etc.), software (e.g., instructions run on a processing device), or a combination thereof. In one embodiment, method 500 is performed by the trial criteria preprocessor 115 of FIG. 2.

At block 505, the trial criteria preprocessor 115 identifies a plurality of unrefined input criteria 120 retrieved from the data store 150. Each of the unrefined input criteria 120 comprises an unrefined textual statement pertaining to one or more medical conditions of one or more patients. At block 510, the trial criteria preprocessor 115 identifies a plurality of already curated output criteria 135 retrieved from the data store 150. Each of the curated output criteria 135 comprises a curated textual statement pertaining to the one or more medical conditions of the one or more patients. At block 515, the trial criteria preprocessor 115 encodes and decodes, using the encoder 125 and the decoder 130, each of the plurality of unrefined input criteria 120 into a corresponding plurality of partially curated output criteria 135, respectively At block 520, the trial criteria preprocessor 115 determines one or more textual differences between each of the partially curated output criteria and a corresponding curated output criterion 135. At block 525, the trial criteria preprocessor 115 applies a training algorithm to the encoder 125 and the decoder 130 to incrementally adjust weights (e.g., $w_1$-$w_n$) of nodes (e.g., $N_1$-$N_n$) within the encoder 125 and the decoder 130 for each of the partially curated output criteria. In one embodiment, the training algorithm is a back propagation neural network training algorithm. If, at block 530, the weights converge based on the determined one or more textual differences for the plurality of partially curated output criteria falling below a predetermined threshold, then processing ceases. If, at block 530, the weights have not yet converged, then processing is repeated using the partially curated output criteria and the already curated output criteria 135 (blocks 515 to 530 are repeated) to re-adjust the weights until the weights converge.

In one embodiment, after a number of input/output criteria have been processed with the trained encoder 125 and decoder 130, the encoder 125 and the decoder 130 may be periodically retrained using the already processed input/output criteria.

Figure 6:
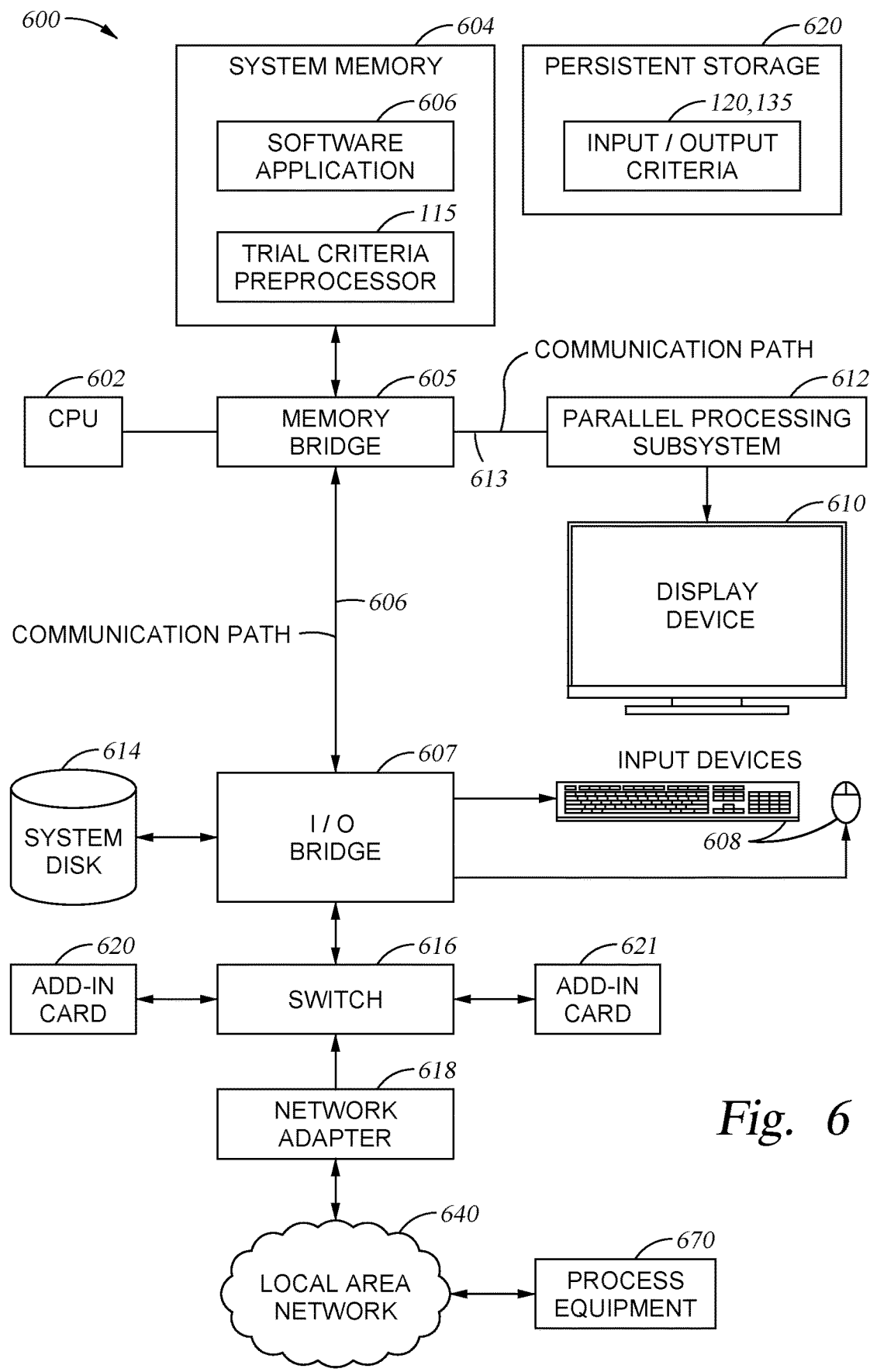
FIG. 6 illustrates an example computing system used for curating clinical trial criteria, according to embodiments of the present disclosure.

FIG. 6 illustrates an example computing system used for curating clinical trial criteria, according to embodiments of the present disclosure. In certain embodiments, computer system 600 is representative of the computer system 100. Aspects of computer system 600 may also be representative of other devices used to perform techniques described herein. For example, computing system 800 may be a personal computer, industrial processor, personal digital assistant, mobile phone, mobile device or any other device suitable for practicing one or more embodiments of the present invention.

The system 600 includes a central processing unit (CPU) 602 and a system memory 604 communicating via a bus path that may include a memory bridge 605. CPU 602 includes one or more processing cores, and, in operation, CPU 602 is the master processor of the system 600, controlling and coordinating operations of other system components. System memory 604 stores a software application 606, and data, for use by CPU 602. CPU 602 runs software applications and optionally an operating system.

Illustratively, the system memory 604 includes trial criteria preprocessor 115, which performs operations related to performing clinical trial criteria formatting of similar computer instructions, according to techniques described herein.

Memory bridge 605, which may be, e.g., a Northbridge chip, is connected via a bus or other communication path (e.g., a HyperTransport link) to an I/O (input/output) bridge 607. I/O bridge 607, which may be, e.g., a Southbridge chip, receives user input from one or more user input devices 608 (e.g., keyboard, mouse, joystick, digitizer tablets, touch pads, touch screens, still or video cameras, motion sensors, and/or microphones) and forwards the input to CPU 602 via memory bridge 605.

A display processor 612 is coupled to the memory bridge 685 via a bus or other communication path (e.g., a PCI Express, Accelerated Graphics Port, or HyperTransport link); in one embodiment display processor 612 is a graphics subsystem that includes at least one graphics processing unit (GPU) and graphics memory. Graphics memory includes a display memory (e.g., a frame buffer) used for storing pixel data for each pixel of an output image. Graphics memory can be integrated in the same device as the GPU, connected as a separate device with the GPU, and/or implemented within system memory 604.

Display processor 612 periodically delivers pixels of the dashboard to a display device 610 (e.g., a screen or conventional CRT, plasma, OLED, SED or LCD based monitor or television). Additionally, display processor 612 may output pixels to film recorders adapted to reproduce computer 600 with an analog or digital signal.

Persistent storage 620 is also connected to I/O bridge 607 and may be configured to store content and applications and data, such as a database library 615, for use by CPU 602 and display processor 612. Persistent storage 620 provides non-volatile storage for applications and data and may include fixed or removable hard disk drives, flash memory devices, and CD-ROM, DVD-ROM, Blu-ray, HD-DVD, or other magnetic, optical, or solid state storage devices. Illustratively, persistent storage 620 includes input, which may comprise the unrefined input criterions 120 and the curated output criterion 135 processed by the trial criteria preprocessor 115.

A switch 616 provides connections between the I/O bridge 607 and other components such as a network adapter 618 and various add-in cards 620 and 621. Network adapter 618 allows the system 600 to communicate with other systems via an electronic communications network, and may include wired or wireless communication over local area networks 640 and wide area networks such as the Internet.

Other components (not shown), including USB or other port connections, film recording devices, or other suitable computing device, may also be connected to I/O bridge 607. For example, process equipment 670 may operate from instructions and/or data provided by CPU 602, system memory 604, or persistent storage 620. Communication paths interconnecting the various components in FIG. 6 may be implemented using any suitable protocols, such as PCI (Peripheral Component Interconnect), PCI Express (PCI-E), AGP (Accelerated Graphics Port), HyperTransport, or any other bus or point-to-point communication protocol(s), and connections between different devices may use different protocols, as is known in the art.

In one embodiment, display processor 612 incorporates circuitry optimized for performing mathematical operations, including, for example, math co-processor, and may additionally constitute a graphics processing unit (GPU). In another embodiment, display processor 612 incorporates circuitry optimized for general purpose processing. In yet another embodiment, display processor 612 may be integrated with one or more other system elements, such as the memory bridge 605, CPU 602, and I/O bridge 607 to form a system on chip (SoC). In still further embodiments, display processor 812 is omitted and software executed by CPU 602 performs the functions of display processor 812.

Pixel data can be provided to display processor 612 directly from CPU 602. In some embodiments, instructions and/or data representing a netlist incremental model verification is provided to set of server computers, each similar to the system 600, via network adapter 618 or system disk 614. The servers may perform operations on subsets of the data using the provided instructions for analysis. The results from these operations may be stored on computer-readable media in a digital format and optionally returned to the system 600 for further analysis or display. Similarly, data may be output to other systems for display, stored in a database library 615 on the system disk 614, or stored on computer-readable media in a digital format.

Alternatively, CPU 602 provides display processor 612 with data and/or instructions defining the desired output images, from which display processor 612 generates the pixel data of one or more output images, including characterizing and/or adjusting the offset between stereo image pairs. The data and/or instructions defining the desired output images can be stored in system memory 604 or graphics memory within display processor 612. CPU 602 and/or display processor 612 can employ any mathematical, function or technique known in the art to create one or more results from the provided data and instructions.

It will be appreciated that the system shown herein is illustrative and that variations and modifications are possible. The connection topology, including the number and arrangement of bridges, may be modified as desired. For instance, in some embodiments, system memory 604 is connected to CPU 602 directly rather than through a bridge, and other devices communicate with system memory 604 via memory bridge 605 and CPU 602. In other alternative topologies display processor 612 is connected to I/O bridge 607 or directly to CPU 602, rather than to memory bridge 605. In still other embodiments, I/O bridge 607 and memory bridge 605 might be integrated into a single chip. The particular components shown herein are optional; for instance, any number of add-in cards or peripheral devices might be supported. In some embodiments, the process equipment 670 may be connected directly to the I/O bridge 607. In some embodiments, the switch 616 is eliminated, and the network adapter 618 and the add-in cards 620, 621 connect directly to the I/O bridge 607.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and processor instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the trial criteria preprocessor 115) or related data available in the cloud. For example, the trial criteria preprocessor 115 could execute on a computing system in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method for correcting errors in textual data, comprising:
    training a first recurrent neural network (RNN) configured as encoder and a second RNN configured as a decoder to improve output accuracy based on an unrefined input criteria containing one or more errors and a corresponding already-curated output criteria, comprising:
        generating a partially-curated output criteria by processing the unrefined input criteria using the first RNN and the second RNN; and
        refining a set of weights of the first RNN and the second RNN based on a difference between the partially-curated output criteria and the already-curated output criteria;
    identifying a first input criterion for the clinical trial, wherein the first input criterion comprises a first textual statement pertaining to a medical condition of a patient, and wherein the first input criterion contains one or more errors;
    encoding the first input criterion using the trained first RNN configured as an encoder, wherein the encoder extracts key features of the medical condition of the patient and converts the key features to a numerical representation;
    generating a curated output criterion by processing the encoded first input criterion with the trained second RNN configured as a decoder, wherein the curated output criterion comprises a second textual statement pertaining to the medical condition of a patient derived from the key features, and wherein the curated output criterion does not contain the one or more errors; and
    improving qualification scoring of a machine learning model by ingesting the curated output criterion into the machine learning model to identify the one or more candidates for the clinical trial, wherein ingesting comprises applying natural language processing to the curated output criterion to extract concepts and logical relationships pertaining to the medical condition of the patient.

2. The method of claim 1, wherein the curated output criterion adheres to a preferred set of logical rules and format.

3. The method of claim 1, wherein the key features comprise a set of attributes of the first statement comprising textual alphanumerical words, and punctuation, and a set of logical rules pertaining to the set of attributes.

4. The method of claim 1, further comprising iteratively training the encoder and the decoder using a plurality of unrefined input criteria associated with a plurality of clinical trials and a corresponding plurality of already-curated output criteria associated with the plurality of clinical trials.

5. The method of claim 4, further comprising:
    identifying the plurality of unrefined input criteria, wherein each of the unrefined input criteria comprises an unrefined textual statement pertaining to one or more medical conditions of one or more patients; and
    identifying the plurality of already-curated output criteria, wherein each of the already-curated output criterial comprises a curated textual statement pertaining to the one or more medical conditions of the one or more patients.

6. The method of claim 5, wherein iteratively training the encoder and the decoder comprises:
    encoding and decoding, using the encoder and the decoder, each of the plurality of unrefined input criteria into a corresponding plurality of partially curated output criteria, respectively;
    determining one or more textual differences between each of the partially curated output criteria and a corresponding curated output criteria;
    applying a training algorithm to the encoder and the decoder to incrementally adjust weights of nodes within the encoder and the decoder for each of the partially curated output criteria; and
    determining whether the weights have converged based on the determined one or more textual differences for the plurality of partially curated output criteria falling below a predetermined threshold.

7. The method of claim 6, further comprising repeating said encoding, said first determining, said applying, and said second determining using the partially curated output criteria and the already-curated output criteria to re-adjust the weights until the weights converge.

8. The method of claim 6, wherein the training algorithm is a back propagation neural network training algorithm.

9. The method of claim 1, further comprising periodically retraining the encoder and the decoder using a collection of unrefined input criteria and curated output criteria already processed by the encoder and the decoder associated with a plurality of clinical trials.

10. The method of claim 1, further comprising providing a minimum size window of text surrounding each word of the input criterion to provide the encoder with a context for the input criterion.

11. A system, comprising:
    a processor; and
    a memory storing program code, which, when executed on the processor, performs operations for correcting errors in textual data, the operations comprising:
        training a first recurrent neural network (RNN) configured as encoder and a second RNN configured as a decoder to improve output accuracy based on an unrefined input criteria containing one or more errors and a corresponding already-curated output criteria, comprising:
            generating a partially-curated output criteria by processing the unrefined input criteria using the first RNN and the second RNN; and
            refining a set of weights of the first RNN and the second RNN based on a difference between the partially-curated output criteria and the already-curated output criteria;
        identifying a first input criterion for the clinical trial, wherein the first input criterion comprises a first textual statement pertaining to a medical condition of a patient, and wherein the first input criterion contains one or more errors;
        encoding the first input criterion using the trained first RNN configured as an encoder, wherein the encoder extracts key features of the medical condition of the patient and converts the key features to a numerical representation;
        generating a curated output criterion by processing the encoded first input criterion with the trained second RNN configured as a decoder, wherein the curated output criterion comprises a second textual statement pertaining to the medical condition of a patient derived from the key features, and wherein the curated output criterion does not contain the one or more errors; and
        improving qualification scoring of a machine learning model by ingesting the curated output criterion into the machine learning model to identify the one or more candidates for the clinical trial, wherein ingesting comprises applying natural language processing to the curated output criterion to extract concepts and logical relationships pertaining to the medical condition of the patient.

12. The system of claim 11, further comprising iteratively training the encoder and the decoder using a plurality of unrefined input criteria associated with a plurality of clinical trials and a corresponding plurality of curated output criteria associated with the plurality of clinical trials.

13. The system of claim 12, further comprising:
    identifying the plurality of unrefined input criteria, wherein each of the unrefined input criteria comprises an unrefined textual statement pertaining to one or more medical conditions of one or more patients; and
    identifying the plurality of curated output criteria, wherein each of the curated output criterial comprises a curated textual statement pertaining to the one or more medical conditions of the one or more patients.

14. The system of claim 13, wherein iteratively training the encoder and the decoder comprises:
    encoding and decoding, using the encoder and the decoder, each of the plurality of unrefined input criteria into a corresponding plurality of partially curated output criteria, respectively;
    determining one or more textual differences between each of the partially curated output criteria and a corresponding curated output criteria;
    applying a training algorithm to the encoder and the decoder to incrementally adjust weights of nodes within the encoder and the decoder for each of the partially curated output criteria; and
    determining whether the weights have converged based on the determined one or more textual differences for the plurality of partially curated output criteria falling below a predetermined threshold.

15. The system of claim 14, further comprising repeating said encoding, said first determining, said applying, and said second determining using the partially curated output criteria and the curated output criteria to re-adjust the weights until the weights converge.

16. A computer program product for correcting errors in textual data, the computer program product comprising:
    a computer-readable storage medium having computer-readable program code embodied therewith, the computer-readable program code executable by one or more computer processors to perform an operation comprising:
        training a first recurrent neural network (RNN) configured as encoder and a second RNN configured as a decoder to improve output accuracy based on an unrefined input criteria containing one or more errors and a corresponding already-curated output criteria, comprising:
            generating a partially-curated output criteria by processing the unrefined input criteria using the first RNN and the second RNN; and refining a set of weights of the first RNN and the second RNN based on a difference between the partially-curated output criteria and the already-curated output criteria;

identifying a first input criterion for the clinical trial, wherein the first input criterion comprises a first textual statement pertaining to a medical condition of a patient, and wherein the first input criterion contains one or more errors;

encoding the first input criterion using the trained first RNN configured as an encoder, wherein the encoder extracts key features of the medical condition of the patient and converts the key features to a numerical representation;

generating a curated output criterion by processing the encoded first input criterion with the trained second RNN configured as a decoder, wherein the curated output criterion comprises a second textual statement pertaining to the medical condition of a patient derived from the key features, and wherein the curated output criterion does not contain the one or more errors; and improving qualification scoring of a machine learning model by ingesting the curated output criterion into the machine learning model to identify the one or more candidates for the clinical trial, wherein ingesting comprises applying natural language processing to the curated output criterion to extract concepts and logical relationships pertaining to the medical condition of the patient.

17. The computer program product of claim 16, the operation further comprising iteratively training the encoder and the decoder using a plurality of unrefined input criteria associated with a plurality of clinical trials and a corresponding plurality of curated output criteria associated with the plurality of clinical trials.

18. The computer program product of claim 17, the operation further comprising:

identifying the plurality of unrefined input criteria, wherein each of the unrefined input criteria comprises an unrefined textual statement pertaining to one or more medical conditions of one or more patients; and identifying the plurality of curated output criteria, wherein each of the curated output criterial comprises a curated textual statement pertaining to the one or more medical conditions of the one or more patients.

19. The computer program product of claim 18, wherein iteratively training the encoder and the decoder comprises:

encode and decode, using the encoder and the decoder, each of the plurality of unrefined input criteria into a corresponding plurality of partially curated output criteria, respectively;

determine one or more textual differences between each of the partially curated output criteria and a corresponding curated output criteria;

apply a training algorithm to the encoder and the decoder to incrementally adjust weights of nodes within the encoder and the decoder for each of the partially curated output criteria; and determine whether the weights have converged based on the determined one or more textual differences for the plurality of partially curated output criteria falling below a predetermined threshold.

20. The computer program product of claim 19, the operation further comprising repeating said encoding, said first determining, said applying, and said second determining using the partially curated output criteria and the curated output criteria to re-adjust the weights until the weights converge.

* * * * *